United States Patent
Ryu et al.

(10) Patent No.: US 9,653,756 B2
(45) Date of Patent: May 16, 2017

(54) MAGNESIUM COMPOUND, ELECTROLYTE SOLUTION FOR MAGNESIUM BATTERY, AND MAGNESIUM BATTERY INCLUDING THE ELECTROLYTE SOLUTION

(71) Applicant: SAMSUNG ELECTRONICS CO., LTD., Suwon-si, Gyeonggi-do (KR)

(72) Inventors: Young-gyoon Ryu, Suwon-si (KR); Seok-soo Lee, Yongin-si (KR); Myung-jin Lee, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 708 days.

(21) Appl. No.: 13/940,411

(22) Filed: Jul. 12, 2013

(65) Prior Publication Data

US 2014/0178773 A1    Jun. 26, 2014

(30) Foreign Application Priority Data

Dec. 21, 2012 (KR) .................. 10-2012-0151339

(51) Int. Cl.
| | | |
|---|---|---|
| *C07F 3/02* | (2006.01) | |
| *H01M 10/0568* | (2010.01) | |
| *H01M 10/054* | (2010.01) | |
| *H01M 10/0567* | (2010.01) | |
| *C07F 3/00* | (2006.01) | |
| *C07F 7/10* | (2006.01) | |
| *H01M 10/0569* | (2010.01) | |

(52) U.S. Cl.
CPC .......... *H01M 10/0568* (2013.01); *C07F 3/003* (2013.01); *C07F 7/10* (2013.01); *H01M 10/054* (2013.01); *H01M 10/0567* (2013.01); *H01M 10/0569* (2013.01)

(58) Field of Classification Search
CPC ................. C07F 3/0032; C07F 7/10
USPC .................. 560/158; 564/82, 159
See application file for complete search history.

(56) References Cited

U.S. PATENT DOCUMENTS

2010/0136438 A1    6/2010 Nakayama et al.

FOREIGN PATENT DOCUMENTS

JP        2007197370 A      8/2007

OTHER PUBLICATIONS

C. Liebenow et al., The electrodeposition of magenisium using solutions of organomagesium halides, amidomagnesium halides and magnesium organoborates, Electrochemistry Communications 2 (2000), pp. 641-645.
T.D. Gregory et al., Nonaqueous Electrochemistry of Magnesium Applications to Energy Storage, J. Eletrochem. Soc., vol. 137, No. 3., Mar. 1990, pp. 775-780.

*Primary Examiner* — Edward Cain
(74) *Attorney, Agent, or Firm* — Cantor Colburn LLP

(57) ABSTRACT

A magnesium compound represented by Formula 1 wherein the magnesium compound is dissolvable in an ether solvent, an electrolyte solution for magnesium batteries that includes the magnesium compound and a magnesium battery including the electrolyte solution are provided:

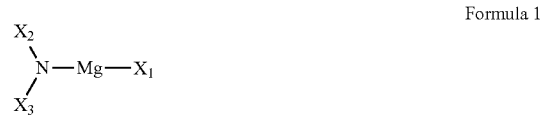

Formula 1 wherein, in Formula 1, $X_1$ is a halogen atom; and at least one of $X_2$ and $X_3$ each independently is an electron withdrawing group, wherein, when $X_2$ or $X_3$ is not an electron withdrawing group, $X_2$ or $X_3$ is a hydrogen atom, a C1-C20 alkyl group, or a C6-C20 aryl group.

17 Claims, 5 Drawing Sheets

MAGNESIUM COMPOUND, ELECTROLYTE SOLUTION FOR MAGNESIUM BATTERY, AND MAGNESIUM BATTERY INCLUDING THE ELECTROLYTE SOLUTION

CROSS-REFERENCE TO RELATED APPLICATIONS

This application claims priority to Korean Patent Application No. 10-2012-0151339, filed on Dec. 21, 2012, and all the benefits accruing therefrom under 35 U.S.C. §119, the content of which in its entirety is herein incorporated by reference.

BACKGROUND

1. Field

This disclosure relates to a magnesium compound, an electrolyte solution for magnesium batteries that includes the magnesium compound, and a magnesium battery including the electrolyte solution, and more particularly, to a magnesium compound that allows reversible dissolution and precipitation of magnesium and may improve the oxidation potential of an electrolyte solution, and an electrolyte solution including the magnesium compound, and a magnesium battery including the electrolyte solution.

2. Description of the Related Art

Recently, there has been an increasing interest in materials for power storage batteries.

Magnesium batteries are environmentally friendly, have competitive pricing, and offer high energy storage characteristics, as compared with existing lithium batteries, lead storage batteries, nickel-cadmium (Ni—Cd) batteries, nickel-hydrogen batteries, and nickel-zinc batteries. Accordingly, magnesium batteries are increasingly being researched.

In general, a magnesium battery includes a cathode containing a metal sulfide active material, such as $Mo_6S_8$, in bulk form, an anode containing a magnesium active material, such as magnesium or an alloy thereof, and an electrolyte solution including a magnesium salt dissolved in an organic solvent.

A common electrolyte solution for magnesium batteries is prepared by dissolving a Grignard magnesium salt and a Lewis acid containing a halogen in an ether solvent. The electrolyte solution contains chemical species formed between magnesium halide cations and organic anions. Such a ligand compound of magnesium halide cations and organic anions has a very low oxidation potential.

Accordingly, electrochemical stability of the electrolyte solution may depend upon oxidation resistance of the magnesium halide cations and the organic anions. In general, a ligand compound of a magnesium halide cations and organic anions has a low oxidation/reduction potential. For this reason, a cathode active material having a low oxidation/reduction potential is used.

When using a cathode active material having a high oxidation/reduction potential to increase energy density of a magnesium battery, decomposition may occur on a surface of the cathode active material due to a side reaction caused by oxidation of the electrolyte solution, which may limit a driving voltage of the magnesium battery.

Therefore, there remains a demand for a magnesium battery including an electrolyte solution that is stable at high voltages.

SUMMARY

Provided is a magnesium compound that allows reversible dissolution and precipitation of magnesium and increases an oxidation potential of an electrolyte solution.

Provided is an electrolyte solution for magnesium batteries that allows reversible dissolution and precipitation of magnesium and has a high oxidation potential.

Provided is a magnesium battery including the electrolyte solution.

Additional aspects will be set forth in part in the description which follows and, in part, will be apparent from the description, or may be learned by practice of the presented embodiments.

According to an aspect of the present disclosure, there is provided a magnesium compound represented by Formula 1 below wherein the magnesium compound is dissolvable in an ether solvent:

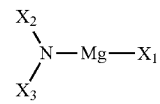

Formula 1 wherein, in Formula 1 above, $X_1$ is a halogen atom; and at least one of $X_2$ and $X_3$ each independently is an electron withdrawing group, wherein, when $X_2$ or $X_3$ is not an electron withdrawing group, $X_2$ or $X_3$ is a hydrogen atom, a C1-C20 alkyl group, or a C6-C20 aryl group.

According to another aspect of the present disclosure, an electrolyte solution for a magnesium battery includes: an ether solvent; and a magnesium compound represented by Formula 1:

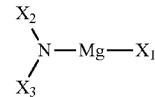

Formula 1 wherein, in Formula 1, $X_1$ is a halogen atom; and at least one of $X_2$ and $X_3$ each independently is an electron withdrawing group, wherein, when $X_2$ or $X_3$ is not an electron withdrawing group, $X_2$ or $X_3$ is a hydrogen atom, a C1-C20 alkyl group, or a C6-C20 aryl group.

In Formula 1, $X_2$ and $X_3$ may be electron withdrawing groups identical to or different from each other.

The electron withdrawing group may be $—C_nF_{2n+1}$ (where 1≤n≤10), $—S(=O)_2C_nF_{2n+1}$ (where 1≤n≤10), —CN, —C(=O)R, —C(=O)OR, or —C(=O)NR, wherein R is a linear or branched C1-C10 alkyl group unsubstituted or substituted with a halogen atom, $—S(=O)_2CF_3$, $—S(=O)_2C_2F_5$, $—C(=O)CH_3$, $—C(=O)OCH_3$, or —CN, or a C6-C10 aryl group unsubstituted or substituted with a halogen atom, $—S(=O)_2CF_3$, $—S(=O)_2C_2F_5$, $—C(=O)CH_3$, $—C(=O)OCH_3$, or —CN.

An amount of the magnesium compound may be from about 0.001M to about 1M.

The electrolyte solution may further include a Lewis acid.

A mole ratio of the magnesium compound to the Lewis acid in the electrolyte solution may be from about 1:1 to about 1:0.001.

The ether solvent may include at least one of an acyclic ether solvent that is unsubstituted or substituted with a halogen atom or a C1-C10 alkyl group, and a heterocyclic ether solvent.

According to another aspect of the present disclosure, a magnesium battery includes one of the above-defined electrolyte solutions; a cathode; and an anode.

The electrolyte solution may have an oxidation potential of about 2.70V or greater versus magnesium.

The electrolyte solution may have an oxidation potential of about 3.00V or greater versus magnesium.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
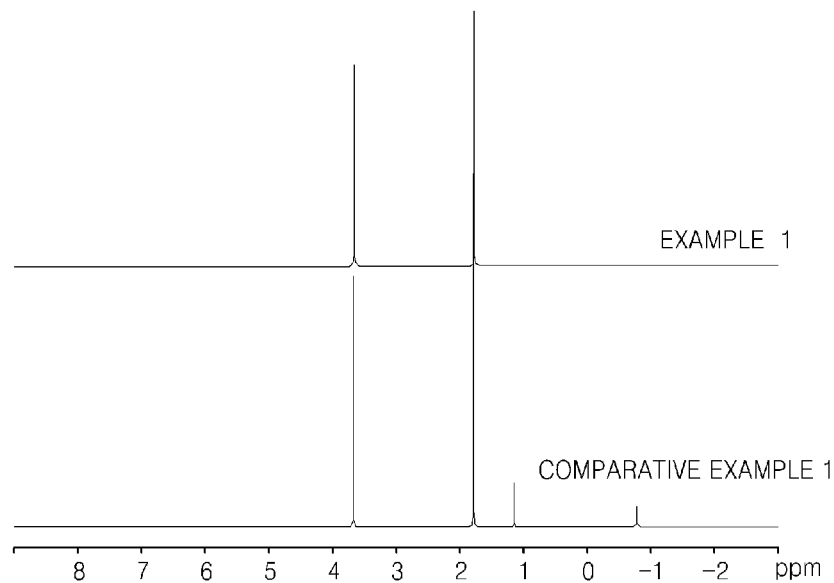
FIG. 1 illustrates $^1$H-NMR spectra of magnesium compounds in electrolyte solutions of Example 1 and Comparative Example 1.

Reference will now be made in detail to embodiments of a magnesium compound, an electrolyte solution for a magnesium battery, and a magnesium battery including the electrolyte solution, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. The term "or" means "and/or." As used herein, the term "and/or" includes any and all combinations of one or more of the associated listed. Expressions such as "at least one of," when preceding a list of elements, modify the entire list of elements and do not modify the individual elements of the list.

It will be understood that when an element is referred to as being "on" another element, it may be directly on the other element or intervening elements may be present therebetween. In contrast, when an element is referred to as being "directly on" another element, there are no intervening elements present. It will be understood that, although the terms first, second, third etc. may be used herein to describe various elements, components, regions, layers and/or sections, there elements, components, regions, layers and/or sections should not be limited by these terms. These terms are only used to distinguish one element, component, region, layer or section from another element, component, Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a", "an" and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, an "alkyl" refers to a straight or branched chain saturated aliphatic hydrocarbon having the specified number of carbon atoms, for example, 1 to 20 carbon atoms, 1 to 12 carbon atoms or 1 to 6 carbon atoms.

An "aryl" refers to a cyclic moiety in which all ring members are carbon and at least one ring is aromatic, the moiety having the specified number of carbon atoms, for example, 6 to 20 carbon atoms or 6 to 12 carbon atoms.

A "halogen" refers to one of the elements of group 17 of the periodic table (e.g., fluorine, chlorine, bromine, and iodine).

A "C1-C10 dialkylboron group" refers to a group represented by —$BR_2$ wherein each R is independently a C1-C10 alkyl group.

A "C6-C12 diarylboron group" refers to a group represented by —BR2 wherein each R is independently a C6 to C12 aryl.

A "C1-C10 alkylcarbonyl group" refers to a group represented by RC(=O)— wherein R is a C1 to C10 alkyl.

A "C1-C10 alkylsulfonyl group" refers to a group represented by RS(=O)— wherein R is a C1 to C10 alkyl.

According to an embodiment, there is provided a magnesium compound represented by Formula 1, wherein the magnesium compound below is dissolvable in an ether solvent:

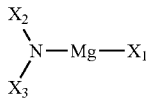

Formula 1

In Formula 1 above, $X_1$ is a halogen atom; and at least one of $X_2$ and $X_3$ each independently is an electron withdrawing group, wherein, when $X_2$ or $X_3$ is not an electron withdrawing group, $X_2$ or $X_3$ is a hydrogen atom, a C1-C20 alkyl group, or a C6-C20 aryl group.

In general, a magnesium compound for a magnesium battery is in the form of an alkyl magnesium halide compound dissolved in an ether solvent. According to Schlenk equilibrium (1), a variety of chemical species may be present in this solution.

$$2(R1)MgX \leftrightarrow (R1)_2Mg + MgX_2 \qquad (1)$$

(wherein R1 is a C1-C10 alkyl group, and X is a halogen atom.)

In Schlenk equilibrium (1) above, $(R1)_2Mg$ has a noncovalent electron pair in carbons of R1, and is highly nucleophilic, and thus is highly vulnerable to oxidation. Accordingly, an electrolyte solution including such a magnesium compound dissolved in an ether solvent may have a low oxidation potential, and thus may lower the energy stability of the electrolyte and the stability of a magnesium battery including the electrolyte solution.

The magnesium compound is a compound dissoluble in an ether solution and not coordinated with a Lewis acid. In the magnesium compound, at least one of $X_2$ and $X_3$ may each independently be an electron withdrawing group. The ether solvent refers to a solvent including an ether bond.

When such a magnesium compound is dissolved and dissociated in an ether solvent, the electron withdrawing group may accept noncovalent electron pairs on carbon of $R_2Mg$ to lower its nucleophilicity. Accordingly, an electrolyte solution including the magnesium compound may allow dissolution and precipitation of magnesium and may have an improved oxidation potential.

In Formula 1 above, $X_2$ and $X_3$ may be electron withdrawing groups identical to or different from each other. A magnesium compound of Formula 1 above where $X_2$ and $X_3$ are electron withdrawing groups identical to or different from each other may be prepared using any one of a variety of methods available in the art.

In some embodiments, the electron withdrawing group may be —$C_nF_{2n+1}$ (where $1 \leq n \leq 10$), —$S(=O)_2C_nF_{2n+1}$ (where $1 \leq n \leq 10$), —CN, —C(=O)R, —C(=O)OR, or —C(=O)NR, wherein R is a linear or branched C1-C10 alkyl group unsubstituted or substituted with a halogen atom, —$S(=O)_2CF_3$, —$S(=O)_2C_2F_5$, —C(=O)CH_3, —C(=O)OCH_3, or —CN, or a C6-C10 aryl group unsubstituted or substituted with a halogen atom, —$S(=O)_2CF_3$, —$S(=O)_2C_2F_5$, —C(=O)CH_3, —C(=O)OCH_3, or —CN, but is not limited thereto. Any of a variety of other electron withdrawing groups known in the art, which do not coordinate with a Lewis acid, may also be used, provided that they may increase the oxidation potential of the magnesium compound.

The magnesium compound of Formula 1 above may include a magnesium compound represented by Formula 2 below:

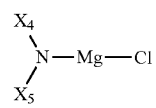

Formula 2

In Formula 2, at least one of $X_4$ and $X_5$ each independently may be —$C_nF_{2n+1}$ (where $1 \leq n \leq 10$), —$S(=O)_2C_nF_{2n+1}$ (where $1 \leq n \leq 10$), —CN, —$C(=O)R_1$, —$C(=O)OR_1$, or —$C(=O)NR_1$, wherein $R_1$ is a linear or branched C1-C10 alkyl group unsubstituted or substituted with a halogen atom, or a C6-C10 aryl group unsubstituted or substituted with a halogen atom.

The magnesium compound of Formula 1 above may include a magnesium compound represented by one of Formulae 3 to 6 below:

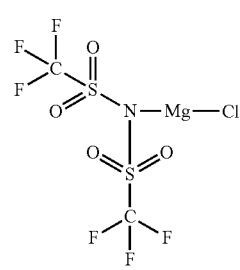

Formula 3

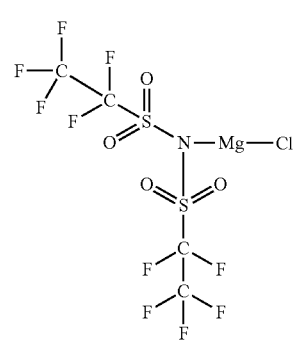

Formula 4

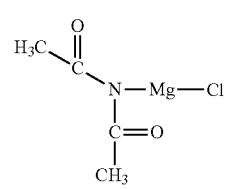

Formula 5

-continued

Formula 6
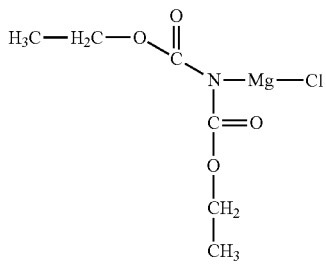

According to another embodiment, there is provided an electrolyte solution for a magnesium battery, the electrolyte solution including: an ether solvent; and a magnesium compound represented by Formula 1 below:

Formula 1
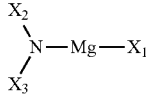

In Formula 1, $X_1$ is a halogen atom; and at least one of $X_2$ and $X_3$ each independently is an electron withdrawing group, wherein, when $X_2$ or $X_3$ is not an electron withdrawing group, $X_2$ or $X_3$ is a hydrogen atom, a C1-C20 alkyl group, or a C6-C20 aryl group.

When the magnesium compound of Formula 1 is dissolved and dissociated in an ether solvent, the electron withdrawing group may accept noncovalent electron pairs of carbanions, bound or unbound with dissociated Mg in the ether solvent to lower nucleophilicity. The electrolyte solution may allow dissolution and precipitation of magnesium and may have an improved oxidation potential.

In Formula 1 above, $X_2$ and $X_3$ may be electron withdrawing groups identical to or different from each other. A magnesium compound of Formula 1 above where $X_2$ and $X_3$ are electron withdrawing groups identical to or different from each other may be prepared using any one of a variety of methods available in the art.

For example, the electron withdrawing group may be —$C_nF_{2n+1}$ where $1 \leq n \leq 10$, —$S(=O)_2C_nF_{2n+1}$ where $1 \leq n \leq 10$, —CN, —C(=O)R, —C(=O)OR, or —C(=O)NR, wherein R is a linear or branched C1-C10 alkyl group unsubstituted or substituted with a halogen atom, —$S(=O)_2CF_3$, —$S(=O)_2C_2F_5$, —C(=O)$CH_3$, —C(=O)$OCH_3$, or —CN, or a C6-C10 aryl group unsubstituted or substituted with a halogen atom, —$S(=O)_2CF_3$, —$S(=O)_2C_2F_5$, —C(=O)$CH_3$, —C(=O)$OCH_3$, or —CN. Other electron withdrawing groups known in the art, which do not coordinated with a Lewis acid, may be used, provided that they may increase the oxidation potential of the magnesium compound.

In some embodiments, the magnesium compound may include a magnesium compound represented by Formula 2 below:

Formula 2
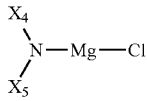

In Formula 2, at least one of $X_4$ and $X_5$ may each independently be —$C_nF_{2n+1}$ (where $1 \leq n \leq 10$), —$S(=O)_2C_nF_{2n+1}$ (where $1 \leq n \leq 10$), —CN, —C(=O)$R_1$, —C(=O)$OR_1$, or —C(=O)$NR_1$, wherein $R_1$ is a linear or branched C1-C10 alkyl group unsubstituted or substituted with a halogen atom, or a C6-C10 aryl group unsubstituted or substituted with a halogen atom.

In some embodiments, the magnesium compound may be a magnesium compound represented by one of Formulae 3 to 6 below:

Formula 3
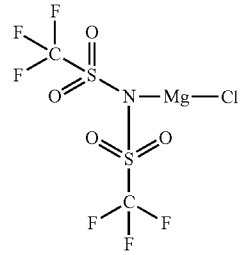

Formula 4
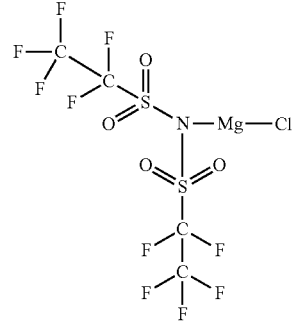

Formula 5
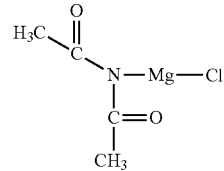

Formula 6
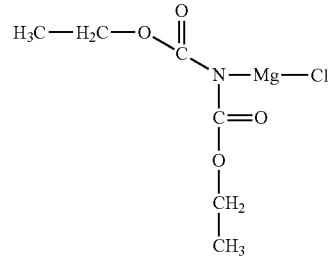

An amount of the magnesium compound may be from about 0.001M to about 1M, from about 0.005M to about 0.5M, from about 0.001M to about 0.1M, from about 0.001M to about 0.05M, from about 0.01M to about 1M, or from about 0.01M to about 0.8M. When the amount of the magnesium compound is within this range, the electrolyte solution may have high magnesium-ion conductivity and may have an appropriate viscosity to form stable electrode/electrolyte interfaces.

In some embodiments, the electrolyte solution may further include at least one magnesium compound selected from R'MgX (where R' is a linear or branched C1-C10 alkyl group, a C6-C10 aryl group, or a linear or branched C1-C10 amine group, and X is a halogen atom), MgX' (where X' is a halogen atom), R"$_2$Mg (where R" is a C1-C10 alkyl group, a C1-C10 dialkylboron group, a C6-C12 diarylboron group, a C1-C10 alkylcarbonyl group, or a C1-C10 alkylsulfonyl group), and MgClO$_4$.

The electrolyte solution may further include a Lewis acid. When the electrolyte solution further includes a Lewis acid, noncovalent electron pairs of carbanions dissociated in the ether solvent may be coordinated by the Lewis acid, which may further stabilize the negative charges of the carbanions. Accordingly, even with a relatively high oxidation potential, the electrolyte solution for a magnesium battery may be less vulnerable to side reactions.

For example, the Lewis acid may include at least one selected from AlCl$_3$, Al(CH$_3$)$_3$, AlH$_3$, Al(OR$_2$)$_3$ (where R$_2$ is a linear or branched C1-C10 alkyl group or a C6-C10 aryl group), Al$^{3+}$, BF$_3$, BCl$_3$, B(OR$_3$)$_3$ (where R$_3$ is a linear or branched C1-C10 alkyl group or a C6-C10 aryl group), R—C=O$^+$ (where R$_3$ is a linear or branched C1-C10 alkyl group or a C6-C10 aryl group), NC$^+$, CO$_2$, R$_4$Si$^+$ (where R$_4$ is a linear or branched C1-C10 alkyl group or a C6-C10 aryl group), Si$^{4+}$, R$_5$PO$^{2+}$ (where R$_5$ is a linear or branched C1-C10 alkyl group or a C6-C10 aryl group), R$_6$OPO$^{2+}$ (where R$_6$ is a linear or branched C1-C10 alkyl group or a C6-C10 aryl group), As$^{3+}$, R$_7$SO$^{2+}$ (where R$_7$ is a linear or branched C1-C10 alkyl group or a C6-C10 aryl group), R$_8$OSO$^{2+}$ (where R$_8$ is a linear or branched C1-C10 alkyl group or a C6-C10 aryl group), SO$_3$, Se$^{3+}$, Cl$^{7+}$, I$^{7+}$, I$^{5+}$, Li$^+$, Na$^+$, K$^+$, Be(CH$_3$)$_2$, Be$^{2+}$, Ca$^{2+}$, Sr$^{2+}$, Ga(CH$_3$)$_3$, Ga$^{3+}$, In(CH$_3$)$_3$, In$^{3+}$, SnR$_9$$^{3+}$ (where R$_9$ is a linear or branched C1-C10 alkyl group or a C6-C10 aryl group), Sn(CH$_3$)$^{2+}$, Sn$^{2+}$, Sc$^{3+}$, La$^{3+}$, Ti(OR$_{10}$)$_4$ (where R$_{10}$ is a linear or branched C1-C10 alkyl group or a C6-C10 aryl group), Ti$^{4+}$, Zr$^{4+}$, VO$^{2+}$, Cr$^{3+}$, Fe$^{3+}$, Co$^{3+}$, Ir$^{3+}$, Th$^{4+}$, UO$_2$$^{2+}$, Pu$^{4+}$, and Tb$^{3+}$.

For example, the Lewis acid may be AlCl$_3$ or BF$_3$.

A mole ratio of the magnesium compound to Lewis acid dissolved in the electrolyte solution may be from about 1:1 to about 1:0.001, from about 1:1 to about 1:0.01, from about 1:1 to about 1:0.1, from about 1:0.5 to about 1:0.001, or from about 1:0.1 to about 1:0.01.

When the mole ratio of the magnesium compound to Lewis acid is within this range, the electrolyte solution may be more electrochemically stable. The mole ratio of the magnesium compound to Lewis acid may be adjusted within a range to have appropriate air-sensitivity and reactivity with a metal, for example, of a current collector in the battery.

The ether solvent may include an acyclic ether solvent that is unsubstituted or substituted with a halogen atom or a C1-C10 alkyl group, and a heterocyclic ether solvent.

In some embodiments, the ether solvent may include at least one selected from 2-methylfuran, tetrahydrofuran, 2-methyltetrahydrofuran, 2,2-dimethyltetrahydrofuran, 2,5-dimethyltetrahydrofuran, 4-methyldioxolane, 1,3-dioxolane, 4,4-dimethyl-1,3-dioxane, dimethylether, dibutylether, polyethyleneglycoldimethylether, 1,2-dimethoxyethane, 1,2-ethoxymethoxyethane, diglyme, methyl diglyme, methyl triglyme, tetraglyme, methyl tetraglyme, ethyl glyme, ethyl diglyme, butyl diglyme, ethyl cellosolve, ethyl carbitol, butyl cellosolve, and butyl carbitol.

In some other embodiments, the ether solvent may include at least one selected from 2-methylfuran, tetrahydrofuran, 2-methyltetrahydrofuran, 2,2-dimethyltetrahydrofuran, 2,5-dimethyltetrahydrofuran, 4-methyldioxolane, 1,3-dioxolane, diglyme, methyl diglyme, methyl triglyme, tetraglyme, methyl tetraglyme, ethyl glyme, ethyl diglyme, and butyl diglyme. For example, the ether solvent may be tetrahydrofuran.

The electrolyte solution may have an oxidation potential of about 2.70V or greater with respect to magnesium, and in some embodiments, about 2.90V or greater with respect to magnesium, and in some other embodiments, about 3.00V or greater with respect to magnesium. The higher the oxidation potential of the electrolyte solution with respect to magnesium, the higher the driving voltage of the magnesium battery may become, and consequently, the higher the energy density of the magnesium battery may become.

According to another embodiment, a magnesium battery includes one of the electrolyte solutions according to the above-described embodiments, a cathode, and an anode.

In some embodiments, the magnesium battery may be manufactured as follows.

First, a cathode is prepared.

For example, a cathode active material, a conducting agent, a binder, and a solvent are mixed to prepare a cathode active material composition. The cathode active material composition may be directly coated on a metallic current collector to prepare a cathode plate. Alternatively, the cathode active material composition may be cast on a separate support to form a cathode active material film, which may then be separated from the support and laminated on a metallic current collector to prepare a cathode plate. The cathode is not limited to the examples described above, and may be one of a variety of types.

The cathode active material of the cathode may include at least one selected from an oxide, a sulfide, and a halide of a metal selected from scandium (Sc), ruthenium (Ru), titanium (Ti), vanadium (V), molybdenum (Mo), chromium (Cr), manganese (Mn), iron (Fe), cobalt (Co), nickel (Ni), copper (Cu), and zinc (Zn); and a magnesium composite metal oxide.

Non-limiting examples of the cathode active material are TiS$_2$, ZrS$_2$, RuO$_2$, Co$_3$O$_4$, Mo$_6$S$_8$, and V$_2$O$_6$. Non-limiting examples of the magnesium composite metal oxide are magnesium compounds represented by the formula of Mg(M$_{1-x}$A$_x$)O$_4$ where $0 \leq x \leq 0.5$, M is Ni, Co, Mn, Cr, V, Fe, Cu, or Ti, and A is Al, B, Si, Cr, V, C, Na, K, or Mg.

The conducting agent may be carbon black or graphite particulates, but is not limited thereto. Any material available as a conducting agent in the art may be used.

Non-limiting examples of the binder are a vinylidene fluoride/hexafluoropropylene copolymer, polyvinylidene fluoride (PVDF), polyacrylonitrile, polymethylmethacrylate, polytetrafluoroethylene, a styrene butadiene rubber polymer, and mixtures thereof, but are not limited thereto. Any material available as a binding agent in the art may be used.

Non-limiting examples of the solvent are N-methyl-pyrrolidone, acetone, and water. Any material available as a solvent in the art may be used.

The amounts of the cathode active material, the conducting agent, the binder, and the solvent are those levels generally used in magnesium batteries. At least one of the conducting agent, the binder, and the solvent may not be used, depending on the use and the structure of the magnesium battery.

Next, an anode is prepared.

The anode of the magnesium battery may include magnesium metal, a magnesium metal-based alloy, a magnesium-intercalating compound, or a combination thereof, but not limited thereto. Any material available as an anode active material in the art that includes magnesium or is capable of intercalating/deintercalating magnesium may be used. The anode determines the capacity of the magnesium battery. In this regard, the anode may be a magnesium metal. Non-limiting examples of the magnesium metal alloy are alloys of magnesium with aluminum (Al), tin (Sn), indium (In), calcium (Ca), titanium (Ti), vanadium (V), and combinations thereof.

For example, the anode may be a magnesium metal having a thickness of from about 3 μm to about 500 μm, from about 50 μm to about 400 μm, from about 100 μm to about 300 μm, or from about 200 μm to about 400 μm, which may be in any of a variety of forms, including a film, a sheet, a foil, a net, a porous structure, foam, and non-woven fabric.

Next, a separator is prepared.

The separator may be additionally disposed between the cathode and the anode of the magnesium battery:

The separator is not specifically limited, and may have any composition durable in an operation environment of the magnesium battery. For example, the separator may be a polymer non-woven fabric, such as polypropylene non-woven fabric, or polyphenylene sulfide non-woven fabric, a porous film of an olefin polymers, such as polypropylene or polyethylene, which may be used in a combination of at least two thereof.

The separator may have low resistance to migration of ions in an electrolyte and have an excellent electrolyte-retaining ability. Examples of the separator are glass fiber, polyester, Teflon, polytetrafluoroethylene (PTFE), or a combination thereof, each of which may be a non-woven or woven fabric.

For example, the separator may be manufactured as follows.

A polymer, a filler, and a solvent may be mixed together to prepare a separator composition. Then, the separator composition may be directly coated on the anode active material layer, and then dried to form the separator. Alternatively, the separator composition may be cast on a support and then dried to form a separator film, which may then be separated from the support and laminated on the anode active material layer to form the separator.

The polymer for manufacturing the separator may be any material that is commonly used as a binder for electrode plates. Non-limiting examples of the polymer are polyethylene, polypropylene, a vinylidenefluoride/hexafluoropropylene copolymer, polyvinylidene fluoride (PVDF), polyacrylonitrile, polymethylmethacrylate, or a combination thereof. The filler for the separator may be, for example, inorganic particles. The solvent may be any of common solvents available in art known as capable of dissolving the polymer and forming pores in the polymer during drying.

In some other embodiments, the separator may be manufactured by any of the methods known in the art, and then laminated on the anode active material layer. In some embodiments, the separator may be manufactured using a dry process, which may involve melting and pressing polypropylene or polyethylene to form a film, annealing the film at a low temperature, growing a crystal domain in the film, drawing the film to extend an amorphous domain in the film, thereby forming a microporous membrane as a separator. In some other embodiments, the separator may be formed using a wet process, which may involve mixing polypropylene or polyethylene with a low-molecular weight material, for example, a hydrocarbon solvent, forming a film from the mixture, the film being embedded with amorphous island phases formed from the solvent or the low-molecular weight material, and removing the island phases of the solvent or low-molecular weight material with another volatile solvent, thereby forming a microporous membrane.

To control the strength or hardness, and thermal shrinkage rate of the separator, an additive, for example, non-conductive particles, a filler, or a fibrous compound may be further added to the separator. For example, the separator may further include inorganic particles. The further inclusion of the inorganic particles may improve oxidation resistance of the separator and suppress deterioration of battery characteristics. For example, the inorganic particles may be alumina ($Al_2O_3$), silica ($SiO_2$), titania ($TiO_2$) particles, or a combination thereof. The inorganic particles may have an average particle diameter of from about 10 nm to about 5 μm. When the average particle diameter of the inorganic particles is less than 10 nm, an effect of adding the inorganic particles may be negligible due to the poor crystalline characteristics of the inorganic particles. When the average particle diameter of the inorganic particle is larger than 5 μm, the inorganic particles may be difficult to diffuse.

To increase the tearing strength and mechanical strength of the separator, the separator may be manufactured to have a multi-layered structure including at least one polymer layer, for example, as a polyethylene/polypropylene laminate, a polyethylene/polypropylene/polyethylene laminate, or a non-woven fabric/polyolefin laminate.

Next, the electrolyte solution as described above is prepared.

The electrolyte solution may be prepared by adding the magnesium compound of Formula 1 into an ether solvent to obtain a solution and mixing the solution to dissolve the magnesium compound, or by further adding a Lewis acid to obtain the solution.

Figure 8:
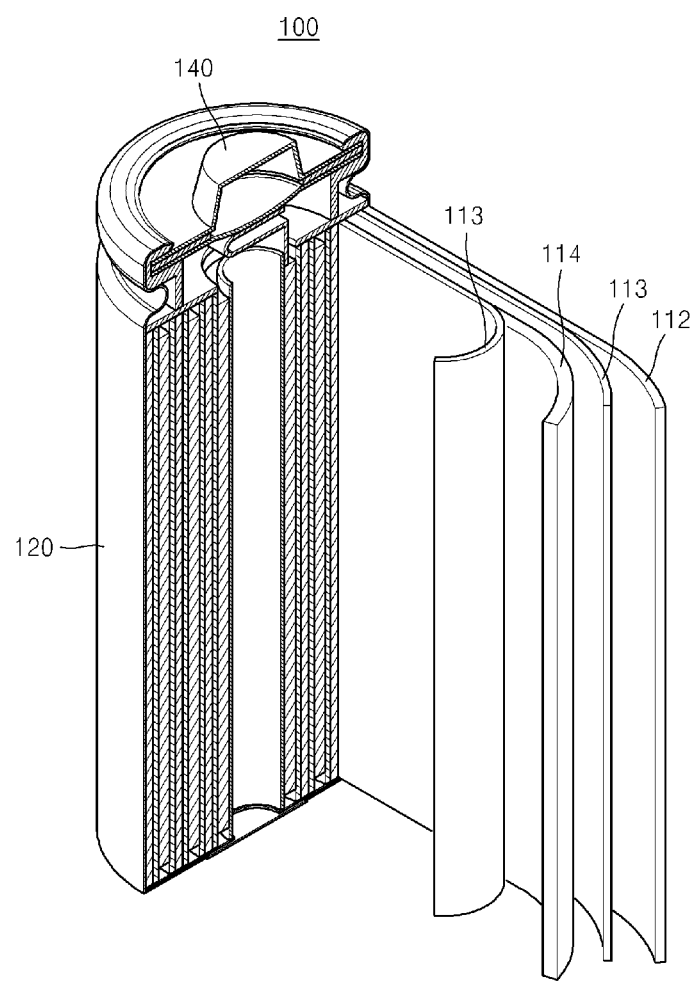
FIG. 8 is a schematic view of an exemplary lithium battery.

Referring to FIG. 8, a magnesium battery 100 according to an exemplary embodiment includes a cathode 114, an anode 112, and a separator 113. The cathode 114, the anode 112, and the separator 113 are wound or folded, and then accommodated in a battery case 120. Subsequently, the electrolyte solution is injected into the battery case 120, and the battery case 120 is then sealed by a sealing member 140, thereby completing the manufacture of the magnesium battery 100. The battery case 120 may be a cylindrical type, a rectangular type, or a thin-film type. In some embodiments, the magnesium battery may be a large thin-film type battery. For example, the magnesium battery may be a magnesium ion battery.

A separator may be interposed between the cathode and the anode to form a battery assembly. Alternatively, the battery assembly may be stacked in a bi-cell structure and impregnated with an organic electrolyte solution. The resultant is put into a pouch and hermetically sealed, thereby completing the manufacture of a magnesium polymer battery.

Alternatively, a plurality of battery assemblies may be stacked to form a battery pack, which may be used in any device that requires high output, for example, in a laptop computer, a smart phone, electric vehicle, and the like.

The magnesium battery may have high storage stability and high thermal stability, and thus may be applicable in an energy storage system (ESS), an electric vehicle (EV), or the like, for example, in a hybrid vehicle such as plug-in hybrid electric vehicle (PHEV).

The embodiments will now be described with reference to the following examples. These examples are for illustrative purposes only and are not intended to limit the scope of the disclosure.

EXAMPLES

Preparation of Magnesium Compound and Electrolyte Solution for Magnesium Battery

Example 1

A 2M ethylmagnesium chloride (C2H5MgCl) solution in anhydrous tetrahydrofuran (THF) (available from Aldrich) was diluted with an appropriate amount of THF to prepare a 0.25M solution. Anhydrous bis(trifluoromethane)sulfonimide (available from Aldrich) was slowly added into the solution to 0.25M while slurring to prepare an electrolyte solution for a magnesium battery, which contains a magnesium compound of Formula 3 below.

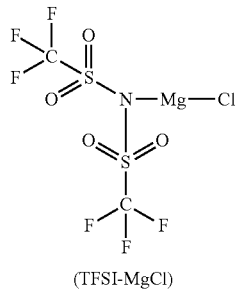

Formula 3

(TFSI-MgCl)

Example 2

An electrolyte solution for magnesium battery, which contains a magnesium compound of Formula 4 below, was prepared as in Example 1, except that bis(pentafluoroethane)sulfonimide (available from Aldrich) instead of bis(trifluoromethane)sulfonimide (available from Aldrich) was slowly added to 0.25M while stirring.

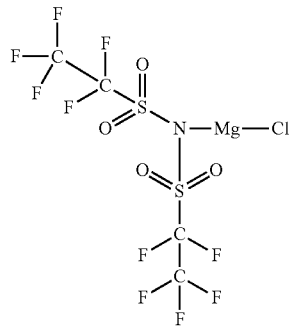

Formula 4

Example 3

An electrolyte solution for a magnesium battery, which contains a magnesium compound of Formula 5 below, was prepared as in Example 1, except that diacetamide (available from Aldrich) instead of bis(trifluoromethane)sulfonimide (available from Aldrich) was slowly added to 0.25M while stirring.

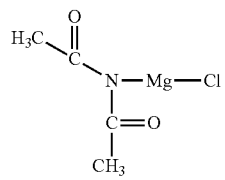

Formula 5

Example 4

An electrolyte solution for a magnesium battery, which contains a magnesium compound of Formula 6 below, was prepared as in Example 1, except that diethyl iminodiacetate (available from Aldrich) instead of bis(trifluoromethane)sulfonimide (available from Aldrich) was slowly added to 0.25M while stirring.

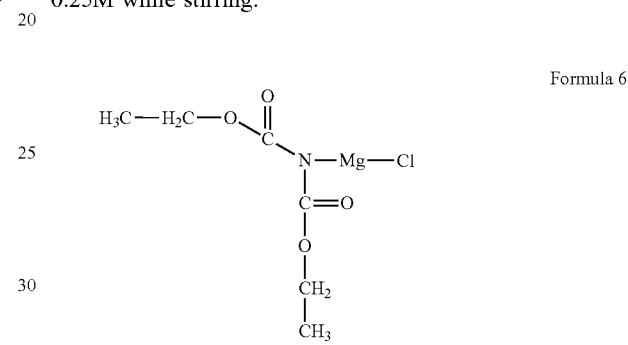

Formula 6

Example 5

A 2M ethylmagnesium chloride (C2H5MgCl) solution in anhydrous tetrahydrofuran (THF) (available from Aldrich) was diluted with an appropriate amount of THF to prepare a 0.25M solution. Anhydrous bis(trifluoromethane)sulfonimide (TFSI available from Aldrich) was slowly added into the solution to 0.25M while slurring to prepare an electrolyte solution for a magnesium battery, which contains a magnesium compound of Formula 3 below.

A solution of AlCl3 in anhydrous THF was mixed with the electrolyte solution which contains the magnesium compound of Formula 3 in a 1:1 mole ratio of AlCl3 to the magnesium compound to prepare an electrolyte solution for a magnesium battery, which contains the magnesium compound of Formula 3 and AlCl3.

Comparative Example 1

A 2M ethylmagnesium chloride (C2H5MgCl) solution in anhydrous tetrahydrofuran (THF) (available from Aldrich) was diluted with an appropriate amount of THF to prepare an electrolyte solution for a magnesium battery, which contains 0.25M ethylmagnesium chloride as a magnesium compound.

Comparative Example 2

A 2M phenylmagnesium chloride (C6H5MgCl) solution in anhydrous tetrahydrofuran (THF) (available from Aldrich) was diluted with an appropriate amount of THF to prepare an electrolyte solution for a magnesium battery, which contains 0.25M phenylmagnesium chloride as a magnesium compound.

Comparative Example 3

A 2M ethylmagnesium chloride ($C_2H_5MgCl$) solution in anhydrous tetrahydrofuran (THF) (available from Aldrich) was diluted with an appropriate amount of THF to prepare a 0.25M solution. Anhydrous hexamethyldisilazane (available from Aldrich) was slowly added into the solution to 0.25M while slurring to prepare an electrolyte solution for a magnesium battery, which contains a magnesium compound of Formula 7 below.

Formula 7

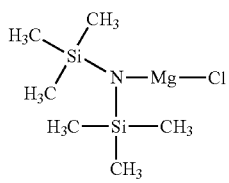

Comparative Example 4

A 2M phenylmagnesium chloride ($C_6H_5MgCl$) solution in anhydrous tetrahydrofuran (THF) (available from Aldrich) was diluted with an appropriate amount of acetone to prepare a 0.25M magnesium compound solution.

A solution of $AlCl_3$ in anhydrous THF was mixed with the magnesium compound solution in a 0.5:1 mole ratio of $AlCl_3$ to the magnesium compound to prepare an electrolyte solution for a magnesium battery which contains phenylmagnesium chloride as a magnesium compound, and $AlCl_3$.

Manufacture of Magnesium Battery

Example 6

$Mo_6S_8$ as a cathode active material, Denka black as a conducting agent, polyvinylidenefluoride (PVdF) as a binder were mixed in a weight ratio of about 80:10:10, followed by adding N-methylpyrrolidone (NMP) and mixing to prepare a cathode active material slurry, which was coated on a SUS foil having a thickness of about 10 μm and dried to obtain a cathode plate.

A coin cell was manufactured from the cathode plate.

The coin cell was manufacturing using a 100 μm-thick magnesium foil as an anode, a 20 μm-thick polyethylene separator (Star® 20), and the electrolyte solution of Example 1.

Examples 7 to 10

Magnesium batteries were manufactured in the same manner as in Example 6, except that the electrolyte solutions of Examples 2 to 5 instead of the electrolyte solution of Example 1 were used, respectively.

Comparative Examples 5 to 8

Magnesium batteries were manufactured in the same manner as in Example 6, except that the electrolyte solutions of Comparative Examples 1 to 4 instead of the electrolyte solution of Example 1 were used, respectively. Identification of components of magnesium compound and electrochemical performance evaluation Evaluation Example 1

$^1$H-NMR Spectrum

The magnesium compounds in the electrolyte solutions of Example 1 and Comparative Example 1 were analyzed by $^1$H-NMR (Avance III 600, Bruker instruments). The results are shown in FIG. 1

Referring to FIG. 1, the magnesium compound in the electrolyte solution of Comparative Example 1 exhibited a $^1$H peak, while the magnesium compound in the electrolyte solution of Example 1 exhibited no $^1$H peak.

Accordingly, the electrolyte solution of Example 1 was found to contain a magnesium compound of Formula 3 below including no $^1$H.

Evaluation Example 2

Oxidation Potential Evaluation (1)

Cyclic voltammetry of the electrolyte solutions of Example 1 and Comparative Examples 1 and 2 were measured at room temperature (25° C.) in a glove box filled with a 99.999% argon gas by using a potentiometer (1287 ECI, Solartron) at a scanning rate of about 10 mV/sec at a voltage range of about −1.0V to about 3.0V with respect to Mg metal.

Figure 2:
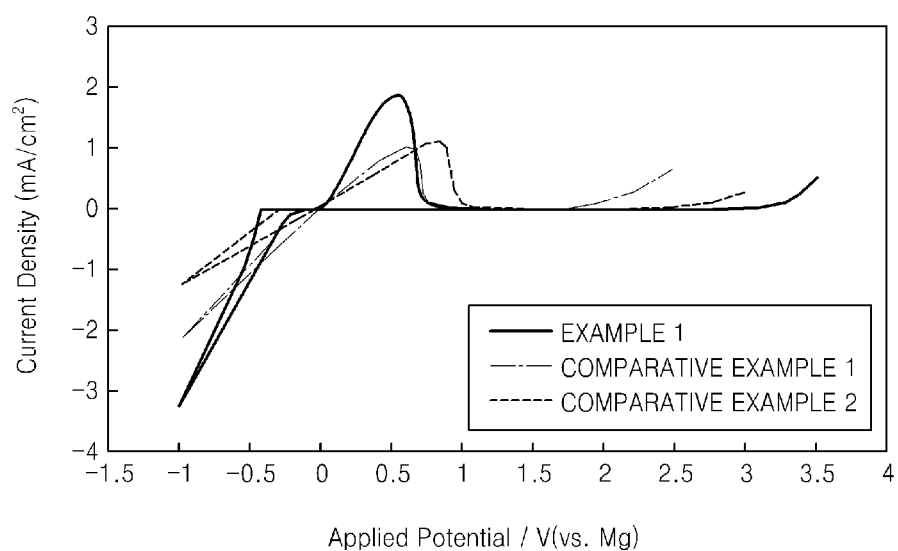
FIG. 2 is a graph of cyclic voltammetry of a triode in the electrolyte solutions of Example 1 and Comparative Examples 1 and 2

A Pt disc electrode was used as a working electrode, and Mg foils were used as a reference electrode and a counter electrode, respectively. The results are shown in FIG. 2 and Table 1 below.

TABLE 1

| | Oxidation potential[$V_{Mg/Mg^{2+}}$] |
|---|---|
| Example 1 | 3.22 |
| Comparative Example 1 | 1.96 |
| Comparative Example 2 | 2.68 |

Cyclic voltammetry of the electrolyte solutions of Example 1 and Comparative Example 3 were measured at room temperature (25° C.) in a glove box filled with a 99.999% argon gas by using the potentiometer at a scanning rate of about 10 mV/sec at a voltage range of about −1.0V to about 3.0V with respect to Mg metal.

Figure 3:
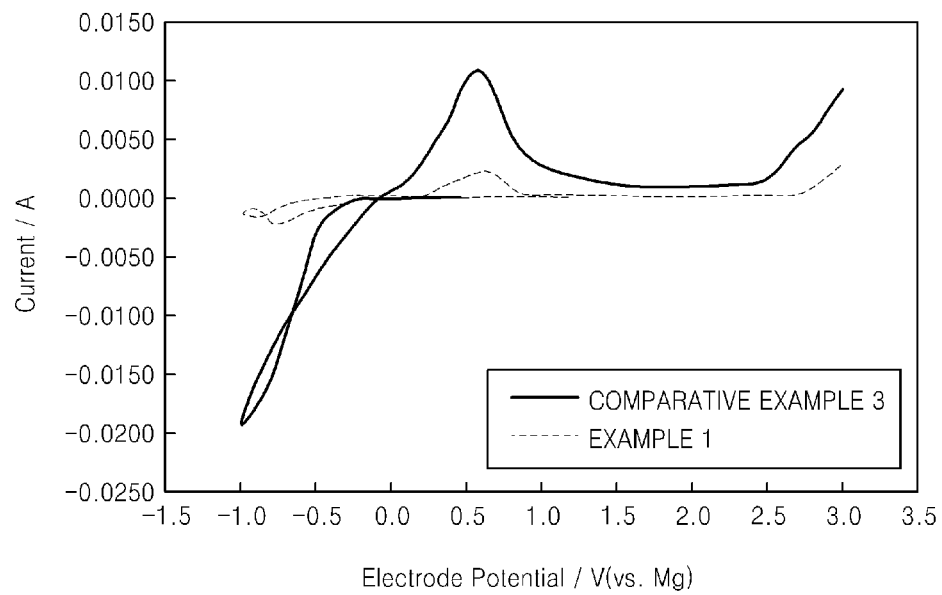
FIG. 3 is a graph of cyclic voltammetry of a two-electrode in the electrolyte solutions of Example 1 and Comparative Example 3.
Figure 4:
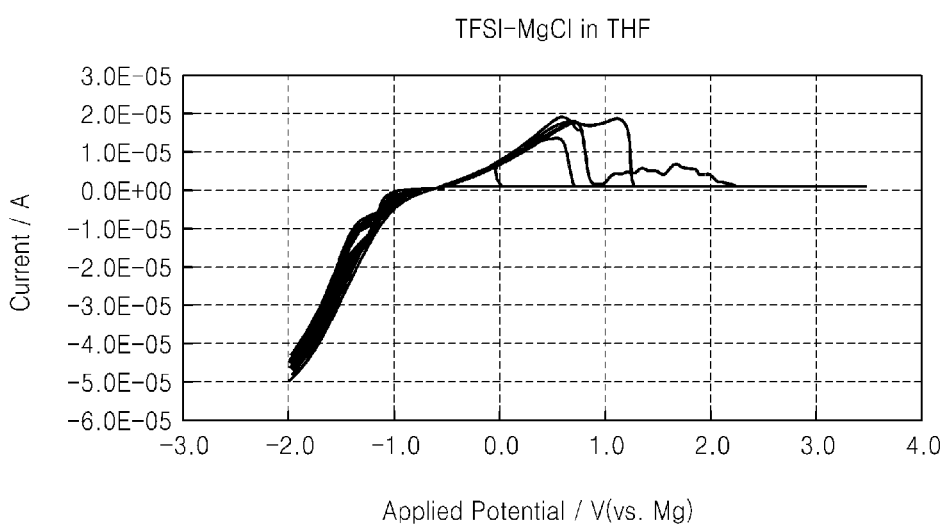
FIG. 4 is a graph of cyclic voltammetry of a triode measuring air-sensitivity in the electrolyte solution of Example 1.
Figure 5:
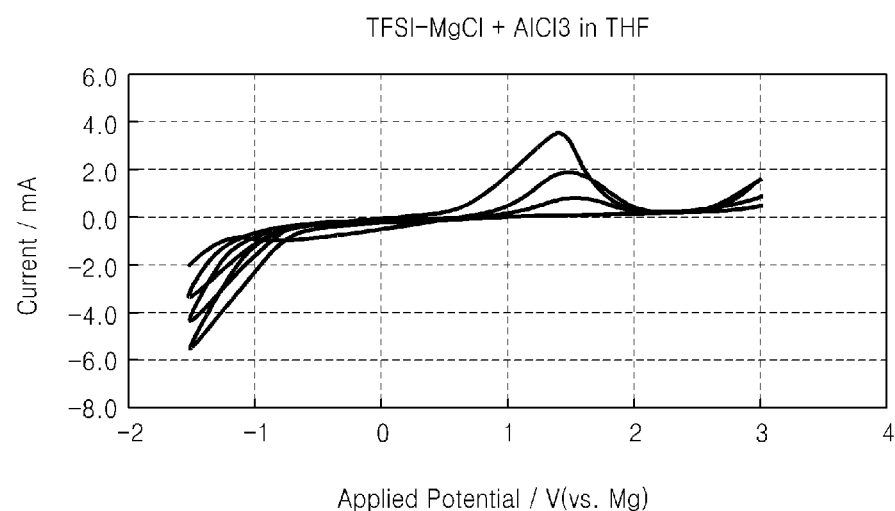
FIG. 5 is a graph of cyclic voltammetry of a triode measuring air-sensitivity in the electrolyte solution of Example 5.
Figure 6:
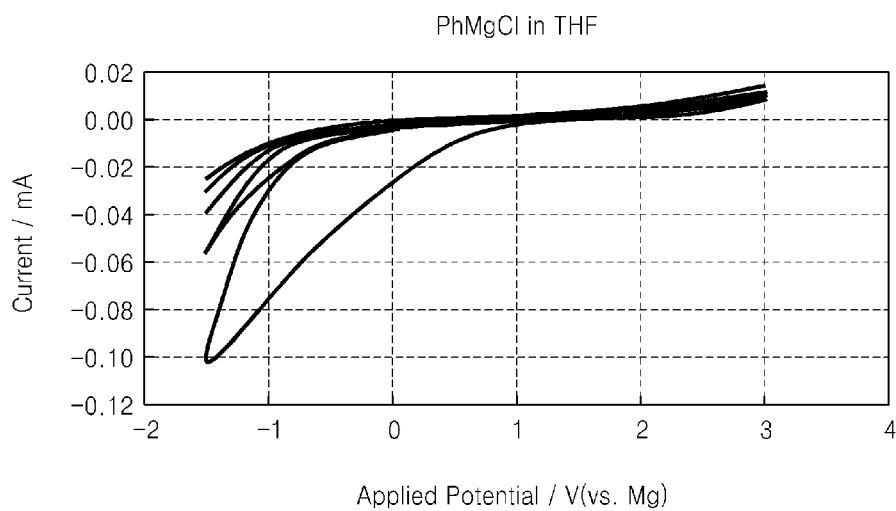
FIG. 6 is a graph of cyclic voltammetry of a triode measuring air-sensitivity in the electrolyte solution of Comparative Example 2.
Figure 7:
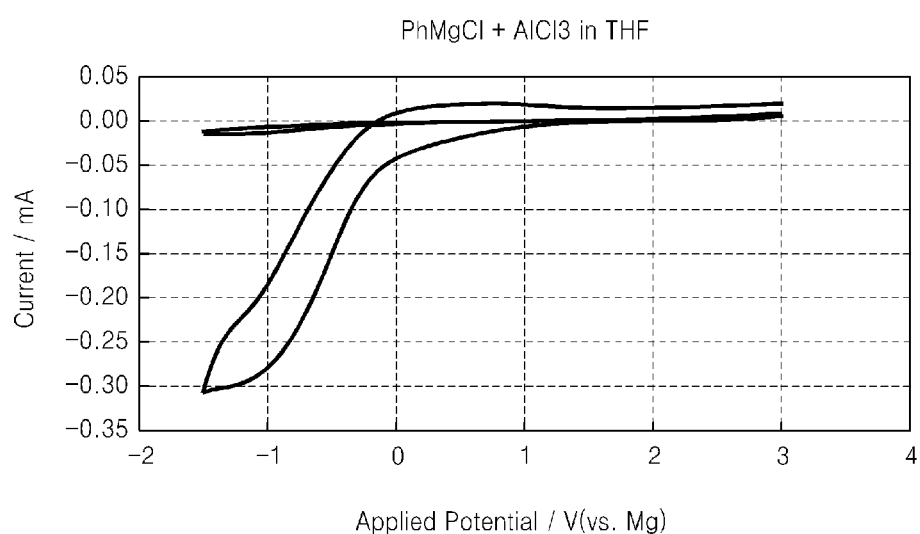
FIG. 7 is a graph of cyclic voltammetry of a triode measuring air-sensitivity in the electrolyte solution of Comparative Example 4.

A stainless steel (SUS) disc electrode was used as a working electrode, and Mg foils were used as a counter electrode, respectively. The results are shown in FIG. 3 and Table 2 below.

TABLE 2

| | Oxidation potential [$V_{Mg/Mg^{2+}}$] |
|---|---|
| Example 1 | 2.73 |
| Comparative Example 3 | 2.47 |

Referring to Table 1 and FIG. 2, the electrolyte solution of Example 1 was found to have an improved oxidation potential as compared with the electrolyte solutions of Comparative Examples 1 and 2.

Referring to Table 2 and FIG. 3, the electrolyte solution of Example 1 was found to have an improved oxidation potential as compared with the electrolyte solution of Comparative Example 3.

These results indicate that when using the electrolyte solution of Example 1, a magnesium battery may use a cathode having a relatively high driving voltage to have a higher energy density, as compared with when using the electrolyte solution of Comparative Example 1 or 2.

Evaluation Example 3

Oxidation Potential Evaluation by Cyclic Voltammetry Measuring Air-Sensitivity

After the electrolyte solutions of Examples 1 and 5 and Comparative Examples 2 and 4 were left in the air for about 5 hours, cyclic voltammetry were measured at room temperature (25° C.) in a glove box filled with a 99.999% argon gas by using a potentiometer (1287 ECI, Solartron) at a scanning rate of about 10 mV/sec at a voltage range of about −1.0V to about 3.0V with respect to Mg metal.

A Pt disc electrode was used as a working electrode, and Mg foils were used as a reference electrode and a counter electrode, respectively. The results are shown in FIGS. 4 to 7.

Referring to FIGS. 4 to 7, even with the exposure to the air, the electrolyte solutions of Examples 1 and 5 were found to allow reversible adsorption and desorption of magnesium. Meanwhile, the electrolyte solutions of Comparative Examples 2 and 4 were found to be deteriorated through reaction with oxygen in the air, and thus failed to ensure reversible adsorption and desorption of magnesium.

Accordingly, when using the electrolyte solution of Example 1 or 5, a magnesium battery may be assembled in the air, which may lower manufacturing costs as compared with a magnesium battery using the electrolyte solution of Comparative Example 2 or 4.

As described above, according to the one or more of the above embodiments of the present disclosure, using an electrolyte solution for a magnesium battery including a magnesium compound of Formula 1 dissolvable in an ether solvent may improve energy density of a magnesium battery.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A magnesium compound represented by Formula 1 wherein the magnesium compound is dissolvable in an ether solvent:

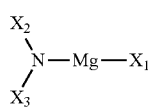

Formula 1 wherein, in Formula 1,
$X_1$ is a halogen atom; and
at least one of $X_2$ and $X_3$ each independently is an electron withdrawing group, wherein the electron withdrawing group is $-C_nF_{2n+1}$ (where $1 \leq n \leq 10$), $-S(=O)_2 C_nF_{2n+1}$ (where $1 \leq n \leq 10$), $-CN$, $-C(=O)R$, $-C(=O)OR$, or $-C(=O)NR$, wherein R is a linear or branched C1-C10 alkyl group unsubstituted or substituted with a halogen atom, $-S(=O)_2CF_3$, $-S(=O)_2 C_2F_5$, $-C(=O)CH_3$, $-C(=O)OCH_3$, or $-CN$, or a C6-C10 aryl group unsubstituted or substituted with a halogen atom, $-S(=O)_2CF_3$, $-S(=O)_2C_2F_5$, $-C(=O)CH_3$, $-C(=O)OCH_3$, or $-CN$.

2. The magnesium compound of claim 1, wherein $X_2$ and $X_3$ are electron withdrawing groups identical to or different from each other.

3. The magnesium compound of claim 1, wherein the magnesium compound comprises a magnesium compound represented by Formula 2:

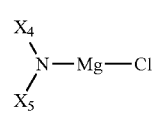

Formula 2 wherein, in Formula 2, at least one of $X_4$ and $X_5$ each independently is $-C_nF_{2n+1}$ (where $1 \leq n \leq 10$), $-S(=O)_2 C_nF_{2n+1}$ (where $1 \leq n \leq 10$), $-CN$, $-C(=O)R_1$, $-C(=O)OR_1$, or $-C(=O)NR_1$, wherein $R_1$ is a linear or branched C1-C10 alkyl group unsubstituted or substituted with a halogen atom, or a C6-C10 aryl group unsubstituted or substituted with a halogen atom.

4. The magnesium compound of claim 1, wherein the magnesium compound comprises a magnesium compound represented by one of Formulae 3 to 6:

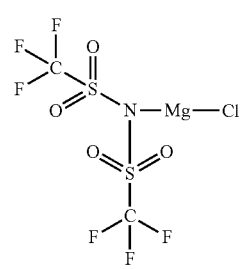

Formula 3

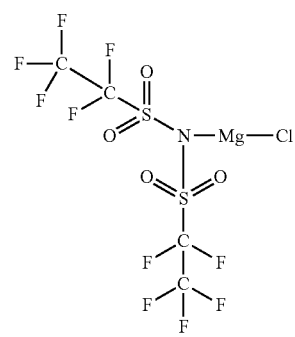

Formula 4

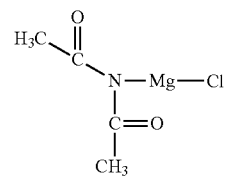

Formula 5

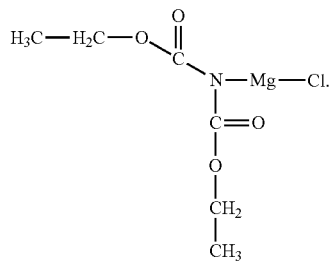

Formula 6

5. An electrolyte solution for a magnesium battery, the electrolyte solution comprising:

an ether solvent; and a magnesium compound represented by Formula 1:

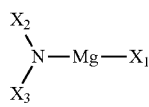

Formula 1 wherein, in Formula 1, $X_1$ is a halogen atom; and at least one of $X_2$ and $X_3$ each independently is an electron withdrawing group, wherein, the electron withdrawing group is $-C_nF_{2n+1}$ (where $1 \le n \le 10$), $-S(=O)_2C_nF_{2n+1}$ (where $1 \le n \le 10$), $-CN$, $-C(=O)R$, $-C(=O)OR$, or $-C(=O)NR$, wherein R is a linear or branched C1-C10 alkyl group unsubstituted or substituted with a halogen atom, $-S(=O)_2CF_3$, $-S(=O)_2C_2F_5$, $-C(=O)CH_3$, $-C(=O)OCH_3$, or $-CN$, or a C6-C10 aryl group unsubstituted or substituted with a halogen atom, $-S(=O)_2CF_3$, $-S(=O)_2C_2F_5$, $-C(=O)CH_3$, $-C(=O)OCH_3$, or $-CN$.

6. The electrolyte solution of claim 5, wherein $X_2$ and $X_3$ are electron withdrawing groups identical to or different from each other.

7. The electrolyte solution of claim 5, wherein the magnesium compound comprises a magnesium compound represented by Formula 2:

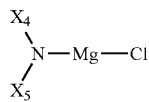

Formula 2 wherein, in Formula 2, at least one of $X_4$ and $X_5$ each independently is $-C_nF_{2n+1}$ (where $1 \le n \le 10$, $-S(=O)_2C_nF_{2n+1}$ (where $1 \le n \le 10$), $-CN$, $-C(=O)R_1$, $-C(=O)OR_1$, or $-C(=O)NR_1$, wherein $R_1$ is a linear or branched C1-C10 alkyl group unsubstituted or substituted with a halogen atom, or a C6-C10 aryl group unsubstituted or substituted with a halogen atom.

8. The electrolyte solution of claim 5, wherein the magnesium compound comprises a magnesium compound represented by at least one of Formulae 3 to 6:

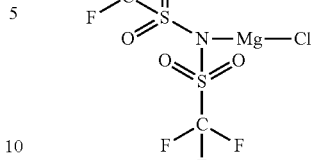

Formula 3

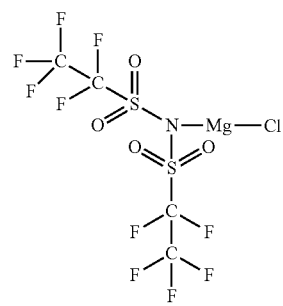

Formula 4

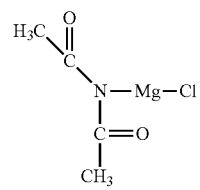

Formula 5

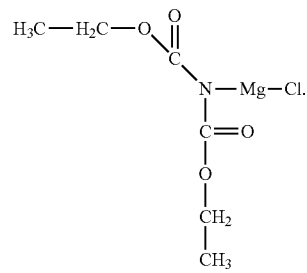

Formula 6

9. The electrolyte solution of claim 5, wherein an amount of the magnesium compound is from about 0.001M to about 1M.

10. The electrolyte solution of claim 5, wherein the electrolyte solution further comprises at least one magnesium compound selected from R'MgX (where R' is a linear or branched C1-C10 alkyl group, a C6-C10 aryl group, or a linear or branched C1-C10 amine group, and X is a halogen atom), MgX' (where X' is a halogen atom), R"$_2$Mg (where R" is a C1-C10 alkyl group, a C1-C10 dialkylboron group, a C6-C12 diarylboron group, a C1-C10 alkylcarbonyl group, or a C1-C10 alkylsulfonyl group), and $MgClO_4$.

11. The electrolyte solution of claim 5, wherein the electrolyte solution further comprises a Lewis acid.

12. The electrolyte solution of claim 11, wherein the Lewis acid comprises at least one selected from $AlCl_3$, $Al(CH_3)_3$, $AlH_3$, $Al(OR_2)_3$ (where $R_2$ is a linear or branched C1-C10 alkyl group or a C6-C10 aryl group), $Al^{3+}$, $BF_3$, $BCl_3$, $B(OR_3)_3$ (where $R_3$ is a linear or branched C1-C10 alkyl group or a C6-C10 aryl group), $R-C=O^+$ (where R is a linear or branched C1-C10 alkyl group or a C6-C10 aryl group), $NC^+$, $CO_2$, $R_4Si^+$ (where $R_4$ is a linear or branched C1-C10 alkyl group or a C6-C10 aryl group), $Si^{4+}$, $R_5PO^{2+}$ (where $R_5$ is a linear or branched C1-C10 alkyl group or a C6-C10 aryl group), $R_6OPO^{2+}$ (where $R_6$ is a linear or branched C1-C10 alkyl group or a C6-C10 aryl group), $As^{3+}$, $R_7SO^{2+}$ (where $R_7$ is a linear or branched C1-C10 alkyl group or a C6-C10 aryl group), $R_8OSO^{2+}$ (where $R_8$ is a linear or branched C1-C10 alkyl group or a C6-C10 aryl group), $SO_3$, $Se^{3+}$, $Cl^{7+}$, $I^{7+}$, $I^{5+}$, $Li^+$, $Na^+$, $K^+$, $Be(CH_3)_2$, $Be^{2+}$, $Ca^{2+}$, $Sr^{2+}$, $Ga(CH_3)_3$, $Ga^{3+}$, $In(CH_3)_3$, $In^{3+}$, $SnR_9^{3+}$ (where $R_9$ is a linear or branched C1-C10 alkyl group or a C6-C10 aryl group), $Sn(CH_3)^{2+}$, $Sn^{2+}$, $Sc^{3+}$, $La^{3+}$, $Ti(OR_{10})_4$ (where $R_{10}$ is a linear or branched C1-C10 alkyl group or a C6-C10 aryl group), $Ti^{4+}$, $Zr^{4+}$, $VO^{2+}$, $Cr^{3+}$, $Fe^{3+}$, $Co^{3+}$, $Ir^{3+}$, $Th^{4+}$, $UO_2^{2+}$, $Pu^{4+}$, and $Tb^{3+}$.

13. The electrolyte solution of claim 11, wherein a mole ratio of the magnesium compound to the Lewis acid in the electrolyte solution is from about 1:1 to about 1:0.001.

14. The electrolyte solution of claim 5, wherein the ether solvent comprises at least one of an acyclic ether solvent that is unsubstituted or substituted with a halogen atom or a C1-C10 alkyl group, and a heterocyclic ether solvent.

15. The electrolyte solution of claim 5, wherein the electrolyte solution has an oxidation potential of about 2.70V or greater versus magnesium.

16. A magnesium battery comprising:
   the electrolyte solution of claim 5;
   a cathode; and
   an anode.

17. The magnesium battery of claim 16, wherein the anode comprises at least one selected from a magnesium metal, a magnesium metal alloy, or a magnesium-intercalating compound.

* * * * *